United States Patent [19]

Blanc

[11] Patent Number: 4,602,106
[45] Date of Patent: Jul. 22, 1986

[54] PROCESS FOR PRODUCING HYDROXYALKYLAMINOACETIC ACIDS

[75] Inventor: Alain Blanc, Paris, France

[73] Assignee: Societe Francaise Hoechst, Puteaux, France

[21] Appl. No.: 713,798

[22] Filed: Mar. 20, 1985

[30] Foreign Application Priority Data

Mar. 26, 1984 [FR] France .............................. 84 04656

[51] Int. Cl.$^4$ ............................................. C07C 99/00
[52] U.S. Cl. .................................... 562/444; 562/567; 544/173
[58] Field of Search ............... 562/443, 567, 575, 444

[56] References Cited

U.S. PATENT DOCUMENTS 2,786,869  3/1957  Benneville et al. ................ 562/567
4,073,804  2/1978  Hearon et al. ...................... 562/575

OTHER PUBLICATIONS

Rakhonankuloo et al., Chem. Abst., vol. 87, #201553c (1977).
Ferruti et al., Chem. Abst., vol. 75, #129,300a (1971).
Laurent et al., Bull Soc. Chim. France, 1978, II pp. 83–88.

*Primary Examiner*—James H. Reamer
*Attorney, Agent, or Firm*—Sheridan Neimark

[57] ABSTRACT

Process for producing hydroxyalkylaminoacetic acids having the general formula (I):

$$R-CHOH-CHR_1-NR_2-CH_2-COOH \quad (I)$$

in which:
R represents a hydrogen atom, a $C_1$-$C_{18}$-alkyl group, with straight or ramified chain, or a phenyl group possibly substituted by one or more radicals (preferably one or two) selected from the group comprising: $C_1$-$C_4$-alkyl, $C_1$-$C_4$-alcoxy or halogeno radicals;
$R_1$ represents a hydrogen atom or a $C_1$-$C_4$-alkyl group;
$R_2$ represents a $C_1$-$C_{18}$-alkyl group or $R_3$—CHOH—CHR$_4$—group in which $R_3$ identical to R represents a hydrogen atom or a $C_1$-$C_{18}$-alkyl group with straight or ramified chain, and $R_4$ is identical to $R_1$, according to which glyoxal is reacted hot upon a secondary hydroxylated amine having the general formula (III):

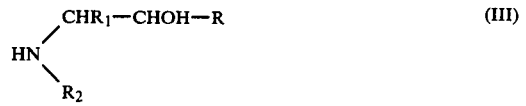

in which R, $R_1$ and $R_2$ have the meaning as given above.

8 Claims, No Drawings

PROCESS FOR PRODUCING HYDROXYALKYLAMINOACETIC ACIDS

This invention relates to a process for producing hydroxyalkylaminoacetic acids.

Hydroxyalkylaminoacetic acids obtained by the process of this invention are products having the general formula (I):

$$R-CHOH-CHR_1-NR_2-CH_2-COOH \quad (I)$$

in which:
- R represents a hydrogen atom, a $C_1$-$C_{18}$-alkyl group with straight or branched chain or a phenyl group possibly substituted by one or several radicals (preferably one or two) selected from $C_1$-$C_4$-alkyl, $C_1$-$C_4$-alkoxy or halogen radicals,
- $R_1$ represents a hydrogen atom or a $C_1$-$C_4$-alkyl group,
- $R_2$ represents a $C_1$-$C_{18}$-alkyl group or $R_3$—CHOH—CHR_4—group in which $R_3$ identical to R represents a hydrogen atom or a $C_1$-$C_{18}$-alkyl group with straight or branched chain and $R_4$ is identical to $R_1$.

The above described substituent groups may moreover be defined as follows:
- a halogen radical comprises: chlorine, bromine, fluorine and iodine. The preferred halogen substituents are chlorine and fluorine,
- a $C_1$-$C_{18}$-alkyl group, with straight or branched chain comprises for example methyl, ethyl, propyl, n-butyl, hexyl, nonyl radicals.

Advantageously, this invention covers a process for obtaining products having the formula (II):

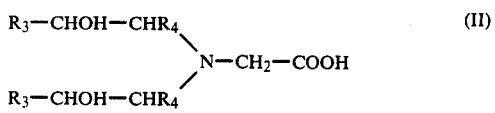

in which $R_3$ represents a hydrogen atom or a $C_1$-$C_{18}$-alkyl radical and $R_4$ represents a hydrogen atom or a $C_1$-$C_4$-alkyl radical.

The object of this invention is more especially a process for producing the following compounds:
N,N-bis-(2-hydroxy,-ethyl)-glycine,
N,N-bis-(2-hydroxy-2-methyl-ethyl)-glycine,
N-methyl-N-(2-hydroxy-ethyl)-glycine,
N-methyl-N-(2-hydroxy-1-methyl-2-phenyl-ethyl)-glycine. Many products having the general formula (I) are described or can be obtained by known means especially, N,N-bis-(2-hydroxy-ethyl)-glycine, which is broadly used for its chelating or complexing properties.

It is known how to obtain N,N-bis-(2-hydroxy-ethyl)-glycine by:
condensation of ethylene oxide with glycine according to A. J. KIPPIANOV, Ukrain. Khim. Zhur., 1926, 2, 236;
hydrolysis of N,N-bis-(2-hydroxy-ethyl)-acetonitrile obtained by Strecker's reaction upon diethanolamine (V. F. LYUBOMUDROV, Ukrain. Khim. Zhur. 1936, 11, 119; A. E. FROST et al., J. Amer. Chem. Soc., 1957, 79, 2755–58; U.S. Pat. Nos. 2,845,457 and 2,860,164);
condensation of chloroacetic acid with diethanolamine according to N. V. KHROMOV-BORISOV et al., Zhur. Obshchei Khim., 1953, 23, 598, and W. S. GUMP et al., J. Org. Chem., 1959, 24, 712–14;
hydrolysis of 4-(2-hydroxy-ethyl)-2-morpholinone, a secondary product, also sometimes a majoritary product obtained upon carrying out the preceding processes (M. L. PASCAL, Bull. Soc. Chim., France, 1960, 435–42 and Compt. Rend., 1957, 245; 1318–20; N. V. KHROMOV-BORISOV et al., loc. cit.).

These methods are general and they may be extended under certain conditions to the preparation of products having the general formula (I) by judicious selection of raw materials. Such is the case for example with cyanomethylation of the hydroxylated secondary amines according to Strecker (U.S. Pat. No. 2,407,645), with condensation according to Hofmann of chloroacetic acid upon secondary amines or else the opening of a suitably chosen epoxide by an amine (M. PASCAL, Compt. Rend. 1957, 244, 1514–16).

It is known moreover from U.S. Pat. No. 3,324,123 how to obtain substituted stituted 2-morpholinones from substituted diethanolamines.

Furthermore, from the technological background it is known that glyoxal admixed cold with N-methyl-N-(2-hydroxy-ethyl)-amine produces apart from the majoritary 3,3'-dimethyl-2,2'-bis-oxazolidine, traces of N-methyl-2-morpholinone (5%), and N-methyl-N-(2-hydroxy-ethyl)-glycine (10%)(P. A. LAURENT et al. Bull. Soc. Chim., France 1978, II, 83-8); on the other hand, on reflux in the presence of a resin KU2, N-butyl or N-phenyl-N-(2-hydroxy-ethyl)-amine leads to 4,8-dibutyl or -diphenyloctahydro-1,4-oxazino-1,4-[3,2-b]-oxazine (D. L. RAKHMANKULOV et al. Soviet Union patent No. 565 034) hydrolyzable into the corresponding glycine (A. le ROUZIC et al. personal communication).

Thus, according to the state of the art, the processes for obtaining products having the general formula (I) require either manipulation of dangerous reactives such as sodium cyanide or ethylene oxide, or long reactional durations (W. S. GUMP et al. loc. cit.), or finally preliminary obtention of the corresponding epoxide.

But there has now been discovered in a completely unexpected manner a novel general process for preparation of the products having the general formula (I), obviating the disadvantages of the known processes, characterized by hot reacting glyoxal with hydroxylated amine having the general formula (III):

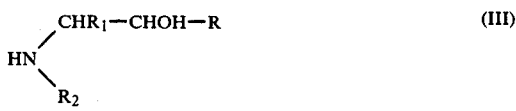

in which R, $R_1$ and $R_2$ have the meaning given above.

Condensation of glyoxal with hydroxylated amine having the general formula (III) is exothermal and it may be schematically shown by equation 1:

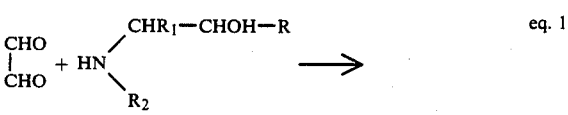

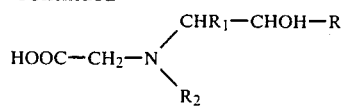

Intermediarily, a lactone of the 2-morpholino type can be formed which easily hydrolyzes into the expected glycine:

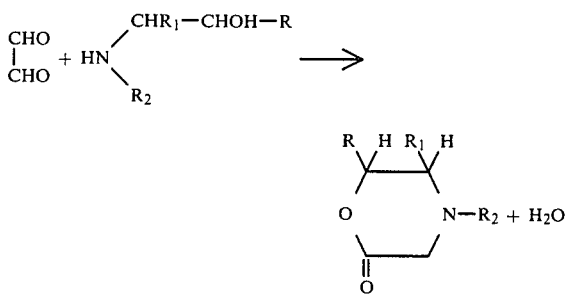

In the crystallized state, the products having the general formula (I) are preferably in form of a dipolar (zwitterion or amphigamous) ion.

As regards operative conditions, the process according to this invention is relatively flexible; thus, if the proportion of one reagent is doubled as compared to the other, the expected glycine yield always remains excellent relative to the reagent present in lesser amount.

Moreover, the process according to the invention is not affected by a strong aqueous dilution or the presence in the reactional medium of one or more alkanols such as methanol, ethanol, ethyleneglycol. However, in concentrated medium with little water, such as can be obtained for example by utilizing crystallized dihydrated trimeric glyoxal (4,4', 5,5'-tetrahydroxy-2,2'-bis-(1,3-dioxolane), according to F. CHASTRETTE et al. Bull. Soc. Chim., France, 1983, II, 33–40), the reactional medium may contain in more or less high proportion a lactone of the 2-morpholinone type, which it is sufficient to heat in the presence of water to generate the expected glycine. Therefore, the process according to the invention is preferentially carried out in aqueous medium and advantageously in the presence of 2.5 to 7.5 moles of water per mole of glyoxal used.

The process according to the invention is realized hot at a temperature higher than 60° C. advantageously, at a temperature of between 80° and 100° and preferably at 100° C.

The reactional duration depends on the temperature and the higher the temperature, the quicker the reactional rate. At 100° C., the reaction is practically completed in one hour. The development of the reaction can be followed by potentiometric dosage of the desired acid from test samples taken regularly from the reactional medium.

Advantageously, glyoxal is utilized in form of its commercial aqueous solutions of 30 to 55% by weight of glyoxal, but it is also possible to use other sources of glyoxal such as 2,3-paradioxanediol or 4,4',5,5'-tetrahydroxy-2,2'-bis-(1,3-dioxolane).

The secondary hydroxylated amines having the general formula (III) are generally known and some of them are even commercialized. Usually, they are obtained by opening an oxirane by ammonia or a primary amine (R.R. WAGNER and H. D. ZOOK, Synthetic Organic Chemistry, 3rd edition, chapter 24, John WILEY and Sons, New York,1961). Such amines are for example diethanolamine, bis-(2-hydroxy-propyl)-amine, bis-(1-methyl-2-hydroxy-ethyl)-amine, bis-(1-ethyl-2-hydroxy-ethyl)-amine, bis-(1,2-dimethyl-2-hydroxyethyl)-amine, bis-(2-hydroxy-1-phenyl-ethyl)-amine, bis-(2-hydroxy-2-phenyl-ethyl)-amine, ethanolisopropanolamine, N-methyl-aminoethanol, ephedrine. The hydroxyaminocarboxylic acids having the general formula (1) obtained by the process according to the invention present precious complexing properties.

The following Examples are given by way of illustration and do not at all limit the invention.

EXAMPLE 1

There is heated for one hour on reflux a solution of:
145 g(1 mole) of glyoxal of 40% by weight in water,
105 g (1 mole) of diethanolamine.

At this stage, potentiometric dosage effected on a test sample determines a yield of 96% of the theoretical value.

The reactional solution is then cooled to the ambient temperature; the desired acid crystallizes spontaneously; it is squeezed out, then dried at 60° C. under vacuum to constant weight.

Thus, there is isolated 105 g(0.65 mole) of N,N-bis-(2-hydroxy-ethyl)-glycine, crystallized, presenting a melting point of 193° C. (literature : 193° C.) and a pK of 8.4, i.e. a yield of 65% of the theoretical value.

Through concentration of mother waters under vacuum to three quarters, there is isolated a second crop of 36 g (0.22 mole) of crystallized N,N-bis-(2-hydroxyethyl)-glycine having a melting point of 193° C., without depression in admixture with the first crop.

The overall yield is determined to 87% of the theoretical value.

A sample recrystallized in water (M=193° C.) presents the following microanalysis:

| | C % | H % | N % |
|---|---|---|---|
| $C_6H_{13}NO_4$ calculated | 44.16 | 8.03 | 8.58 |
| M.W. 163.16 found | 43.9 | 8.5 | 8.6 |

EXAMPLE 2

There is heated for one hour on reflux a solution of:
145 g (1 mole) of glyoxal of 40% by weight in water;
105 g (1 mole) of diethanolamine;
200 cm$^3$ of ethanol.

At this stage potentiometric dosage gives a yield of 85% of the theoretical value.

The reactional solution is then cooled to the ambient temperature. The desired product crystallizes spontaneously. It is squeezed out and dried to constant weight under vacuum at 60° C. Thus, there is isolated a first crop of 82 g (0.5 mole) of crystallized N,N-bis-(2-hydroxy-ethyl)-glycine having a melting point of 193° C. The mother waters concentrated under vacuum up to half the volume are left to deposit a second crop of 41 g (0.25 mole) of N,N-bis-(2-hydroxy-ethyl)-glycine crystallized (193° C.).

The overall yield is determined to 75% of the theoretical value.

EXAMPLE 3

Into 120 g (1 mole) of 2,3-paradioxanediol previously molten and then maintained at 80° C., there is introduced under stirring in 30 minutes:

105 g (1 mole) of diethanolamine, then the solution is heated for 1 hour to 100° C.

At this stage, potentiometric dosage gives a yield of 95% of the theoretical value.

The reactional solution is then cooled to the ambient temperature; it sets to a mass. It is caused to slack under stirring with 175 cm³ of methanol and the obtained product, crystallized, is squeezed out and thereafter dried under vacuum at 60° C. to constant weight.

There is thus isolated 120.7 g (0.74 mole) of N,N-bis-(2-hydroxy-ethyl)-glycine having a melting point of 193° C.

The overall yield is determined to 74% of the theory.

EXAMPLE 4

There is heated for 1 hour on reflux a solution of:
210.14 g (1 mole) of crystallized 4,4',5,5'-tetrahydroxy-2,2'-bis-(1,3-dioxolane) commercialized under the name of crystallized hydrate glyoxal;
105 g (1 mole) of diethanolamine;
150 cm³ of methanol,
then the reactional medium is concentrated dry under vacuum.

The residual oil analyzed by infrared spectrography shows that it is constituted by a mixture of N,N-bis-(2-hydroxy-ethyl)-glycine and N-(2-hydroxy-ethyl)-2-morpholone, characterized by their absorption in the carbonyl regions:

$vc = 0 \ 1735 \ cm^{-1}$ lactone $vc = 0 \ 1650 \ cm^{-1}$ carboxylate ion.

This oil is heated for 1 hour on reflux in two volumes of water.

At this stage, potentiometric dosage effected on a test sample shows the presence of 96% of the desired glycine.

The reactional medium is then cooled to the ambient temperature; the desired acid crystallizes spontaneously; it is squeezed out, then dried at 60° C. under vacuum to constant weight.

Thus, there is isolated 137 g (0.84 mole) of N,N-bis-(2-hydroxy-ethyl)-glycine having a melting point of 193° C.

EXAMPLE 5

There is heated for 1 hour in reflux a solution of:
145 g (1 mole) of glyoxal at 40% by weight in water;
210 g (2 moles) of diethanolamine;

At this stage, potentiometric dosage effected on a test sample permits to conclude to a yield of 90% of the theoretical value.

Then, the reactional solution is treated as in Example 1. There is thus isolated a first crop of 73.4 g (0.45 mole) of crystallized N,N-bis-(2-hydroxy-ethyl)-glycine having a melting point of 193° C. It has not been attempted to isolate a second crop.

EXAMPLE 6

There is heated for 1 hour in reflux a solution of:
290 g (2 moles) of glyoxal at 40% by weight of water;
105 g (1 mole) of diethanolamine;

At this stage potentiometric dosage effected on a test sample leads to a yield of 95% of the theoretical value.

Then, the reactional solution is treated as in Example 1. There is thus isolated a first crop of 90 g (0.55 mole) of crystallized N,N-bis-(2-hydroxy-ethyl)-glycine having a melting point of 193° C. It has not been attempted to isolate a second crop.

EXAMPLE 7

There is heated for 1 hour in reflux a solution of:
145 g (1 mole) of glyoxal at 40% by weight in water;
133.2 g (1 mole) of bis-(2-hydroxy-propyl)-amine.

At this stage, potentiometric dosage effected on a test sample permits to conclude to a yield of 93% of the theoretical value.

The reactional solution is then treated as in Example 1. There is isolated thus in two crops 155 g (0.81 mole) of N,N-bis-(2-hydroxy-propyl)-glycine presenting a melting point of 145° C. and a pKa of 8.2 (Literature: M. L. PASCAL, Bull. Soc. Chim., France, 1960, II, 435–42, m.p. = 145°–146° C.)

The overall yield is established to 81% of the theoretical value.

EXAMPLE 8

There is heated for 1 hour in reflux a solution of:
29 g (0.2 mole) of glyoxal at 40% by weight in water;
33 g (0.2 mole) of racemic ephedrine;
155 cm³ of ethanol;
200 cm³ of water,
then the ethanol is distillated under vacuum and the heating on reflux is continued for 1 hour.

At this stage, potentiometric dosage effected on a test sample reveals the presence of 100% of the desired acid.

The aqueous solution is then concentrated dry under vacuum; the residual oil is impasted on reflux in 250 cm³ of isopropanol, then it is left for 3 hours at 0° C. The crystallized precipitate is then squeezed out and thereafter dried under vacuum at 60° C. to constant weight.

There is thus isolated 30 g (0.135 mole) of crystallized N-methyl-N-(2-hydroxy-1-methyl-2-phenyl-ethyl)-glycine having a melting point of 163° C.

The overall yield represents 67% of the theoretical value.

| | Microanalysis. | | |
| --- | --- | --- | --- |
| | C % | H % | N % |
| $C_{12}H_{17}NO_3$ calculated | 64.55 | 7.68 | 6.27 |
| M.W. 223.3 found | 64.5 | 7.8 | 6.1 |

To the Applicant's knowledge, this product was not described in the literature.

EXAMPLE 9

There is heated for 1 hour on reflux a solution of:
145 g (1 mole) of glyoxal in aqueous solution at 40% by weight;
75.1 g (1 mole) of methyl-ethanolamine;
100 g of water.

At this stage potentiometric dosage effected on a test sample shows the presence of 99% of the desired acid.

The solution is then concentrated under vacuum so as to eliminate 82 g of water, then the reactional medium is left to crystallize for 16 hours at the ambient temperature.

Thereafter, the obtained crystallized mass is caused to slack with 250 cm³ of ethanol, then it is squeezed out and the recovered product is then dried at 60° C. under vacuum to constant weight.

There is thus isolated 99 g (0.74 mole) of crystallized N-methyl-N-(2-hydroxy-ethyl)-glycine having a melting point of 132° C. (Literature: E. KNORR et al., Annalen, 1899, 307, 201; m.p.=132°-133° C.)

EXAMPLE 10

There is heated for 1 hour on reflux a solution of:
14.5 g (0.1 mole) of glyoxal at 40% by weight in water;
25.7 g (0.1 mole) of 2-tetradecylamino-ethanol in 100 cm³ of ethanol.

At this stage a sample analyzed by infrared spectrography shows the presence of a lactone function. There is introduced into the reactional medium 160 g of water, then reflux is continued for 2 hours.

The reactional solution is then concentrated under vacuum, and the desired acid crystallizes. It is isolated, then recrystallized under hot and cold conditions in dioxane.

There is thus obtained 24.1 g of crystallized N-(2-hydroxy-ethyl)-N-tetradecyl-glycine having a melting point of 95° C., i.e. a yield of 76.5% of the theoretical value.

|  | Microanalysis. | | | |
| --- | --- | --- | --- | --- |
|  | C % | H % | N % | O % |
| $C_{18}H_{37}NO_3$ calculated | 68.52 | 11.82 | 4.44 | 15.21 |
| MW = 315.5 found | 68.6 | 12.4 | 4.2 |  |

It will be understood that this invention was only described in a purely explanatory and not at all limitative manner and that any useful modification can be introduced thereinto without however departing from its scope as defined in the appended claims.

I claim:

1. A process for producing hydroxyalkylaminoacetic acid of the formula (I):

$$R-CHOH-CHR_1-NR_2-CH_2-COOH \quad (I)$$

wherein
R is hydrogen, $C_1$-$C_{18}$ alkyl or phenyl which is optionally substituted by at least one radical selected from the group consisting of halogen, $C_1$-$C_4$ alkyl and $C_1$-$C_4$ alkoxy;
$R_1$ is hydrogen or $C_1$-$C_4$ alkyl;
$R_2$ is hydrogen, $C_1$-$C_{18}$ alkyl or the radical R'—CHOH—CHR$_1$ in which R' is hydrogen or $C_1$-$C_{18}$ alkyl, and $R_1$ has the meaning given above;
said process comprising hot reacting, in the absence of catalyst, an aqueous solution of glyoxal with a secondary hydroxylate amine having the formula (III):

$$R_2NH-CHR_1-CHOHR \quad (III)$$

in which R, $R_1$ and $R_2$ have the meaning given above.

2. A process according to claim 1, wherein the hydroxyalkylaminoacetic acid is an acid having the formula:

$$(R_3CHOH-CHR_4)_2 N-CH_2-COOH$$

wherein
$R_3$ is hydrogen or $C_1$-$C_{18}$ alkyl;
$R_4$ is hydrogen or $C_1$-$C_4$ alkyl; and the secondary hydroxylated amine has the formula:

$$HN(CHR_4-CHOHR_3)_2$$

in which $R_3$ and $R_4$ have the meaning given above.

3. A process according to claim 1, wherein the reaction occurs at a temperature higher than 60° C.

4. A process according to claim 1, wherin one mole of glyoxal is reacted at a temperature of between 60° and 100° C. in aqueous solution upon one mole of secondary hydroxylated amine havint the general formula(III).

5. A process according to claim 2, wherein said hydroxyalkylaminoacetic acid is N-methyl-N-(2-hydroxyethyl)-glycine.

6. A process according to claim 1 wherein hydroxyalkylaminoacetic acid is N-methyl-N-(2-hydroxy-1-methyl-2-phenyl)-glycine.

7. A process according to claim 2, wherein said hydroxyalkylaminoacetic acid is N,N-bis-(2-hydroxyethyl)-glycine.

8. A process according to claim 2, wherein said hydroxyalkylaminoacetic acid is N,N-bis-(2-hydroxy-2-propyl)-glycine.

* * * * *